United States Patent [19]
Naik et al.

[11] Patent Number: 5,284,856
[45] Date of Patent: Feb. 8, 1994

[54] ONCOGENE-ENCODED KINASES INHIBITION USING 4-H-1-BENZOPYRAN-4-ONE DERIVATIVES

[75] Inventors: Ramchandra G. Naik; Bansi Lal, both of Bombay, India; Richard H. Rupp, Königstein/Taunus, Fed. Rep. of Germany; Hans H. Sedlacek, Marburg, Fed. Rep. of Germany; Gerhard Dickneite, Marburg, Fed. Rep. of Germany

[73] Assignee: Hoechst Aktiengesellschaft, Frankfurt am Main, Fed. Rep. of Germany

[21] Appl. No.: 924,595

[22] Filed: Jul. 24, 1992

Related U.S. Application Data

[63] Continuation of Ser. No. 622,116, Dec. 6, 1990, abandoned, which is a continuation of Ser. No. 426,543, Oct. 26, 1989, abandoned.

[30] Foreign Application Priority Data

Oct. 28, 1988 [DE] Fed. Rep. of Germany ....... 3836676

[51] Int. Cl.$^5$ .......................................... A61K 31/445
[52] U.S. Cl. ..................................... 514/320; 514/318
[58] Field of Search ................................ 514/320, 318

[56] References Cited

U.S. PATENT DOCUMENTS

| | | | |
|---|---|---|---|
| 3,629,290 | 12/1971 | Cairns | 549/402 |
| 4,603,137 | 7/1986 | Bhat et al. | 514/320 |
| 4,900,727 | 2/1990 | Kattige | 514/212 |

FOREIGN PATENT DOCUMENTS 0366061 10/1989 European Pat. Off. .

OTHER PUBLICATIONS

Mutschler, E., "Arzneimittelwirkungen: Lehrbuch der Pharmakologie und Toxikologie: mit einfuhrenden Kapiteln in die Anatomie, Physiologie und Pathophysiologie", Wissenschaftliche Verlagsgesellschaft, Stuttgart, 1991, pp. 656–661.

Murray, K., et al., "Protein Kinases, in Hensch, C., Comprehensive M.C.", pp. 531–533. (date not available and cannot be acertained).

Organikum [Laboratory Practice in Organic Chemistry], VEB, Deutscher Verlag der Wissenschaften, 15th edition, Berlin 1977, Chapter D7, pp. 475–477.

Chemical Abstracts 108 183888m, 1988, p. 438.
Chemical Abstracts 106 38467c, 1987, p. 359.

*Primary Examiner*—Mary C. Lee
*Assistant Examiner*—Jacqueline Haley
*Attorney, Agent, or Firm*—Finnegan, Henderson, Farabow, Garrett & Dunner

[57] ABSTRACT

Compounds of the formula I

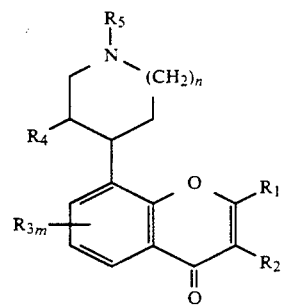

in which the substituents $R_1$–$R_5$ and n and m are as defined are suitable for controlling tumors.

3 Claims, No Drawings

ONCOGENE-ENCODED KINASES INHIBITION USING 4-H-1-BENZOPYRAN-4-ONE DERIVATIVES

This application is a continuation of application Ser. No. 07/622,116, filed Dec. 6, 1990, now abandoned, which is a continuation of Ser. No. 07/426,543, filed Oct. 26, 1989, now abandoned.

The present invention relates to the use of 4H-1-benzopyran-4-one derivatives, to novel 4H-1-benzopyran-4-one derivatives, and to phamaceuticals containing them.

Benzopyran derivatives have already been described in European Patent Specification No. 0,137,193 (equivalent to U.S. Pat. No. 4,603,137) and in German Offenlegungsschrift 3,612,337 (equivalent to U.S. Pat. No. 4,900,727). The latter discloses compounds of the formula a).

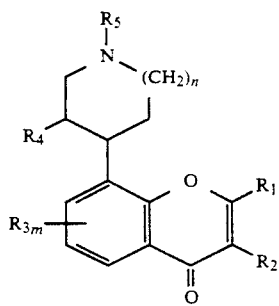

in which the substituents $R_1$ to $R_5$ and m and n are as defined; the compounds have an antiinflammatory analgesic and immune-modifying action.

Surprisingly, it has not been found that certain 4H-1-benzopyran-4-one derivatives inhibit oncogene-encoded kinases and are therefore suitable for controlling tumoral diseases.

The expression of oncogenes in a mammalian cell entails transition from the normal cell type to the transformed cell type, which then becomes a cancer cell. The transformation was caused by infecting a cell with a retro-virus. A well known example was the infection of chickens with Rous-sarcoma virus, and these chickens then developed cancer. The corresponding oncogene, which was responsible for the malign transformation, was named "SRC" (sarcoma) gene (J. S. Brugge, R. L. Erikson; Nature 269, 346-348 (1977)). A characteristic feature of many oncogenes known to date is the expression of a protein having kinase activity. The enzymes catalyze the transfer of the terminal phosphate group of ATP to an amino acid. In contrast to many other protein kinases which transfer the phosphate group to a seryl radical or threonyl radical, most of the oncogene-encoded kinases phosphorylate a tyrosyl radical of the protein chain. Besides, it is known that products of oncogenes, namely those of the v-mos, v-mil and v-raf oncogenes, have serin/threonin-specific protein kinase activity. (K Mölling et al., Nature (London) 312, 558-561 (1984); B. Singh et al., Journal of Virology 60, 1149-1152 (1986)).

Tyrosin kinase activity is also expressed in growth factor receptors; new findings now show that the growth of many tumors is dependent on the presence of growth factors, such as Epidermal Growth Factor (EGF), Transforming Growth Factor α (TGFα) or Platelet Derived Growth Factor (POGF) (A. S. Goustin, G. D. Shipley, H. L. Moses, Cancer Research 46, 1015-1029 (1986). Once the growth factor is bound to its receptor, tyrosin kinase, which is an intrinsic component of the growth factor receptor, is stimulated.

A tyrosin kinase inhibitor and possibly a serin/threonin kinase inhibitor might therefore inhibit the growth and spreading of tumors, and it could be employed in tumor therapy.

The present invention therefore relates to the use of 4H-1-benzopyran-4-one derivatives of the formula I for inhibiting oncogene-encoded kinases and growth factor receptor tyrosin kinases and for the control of tumoral diseases. Formula I reads

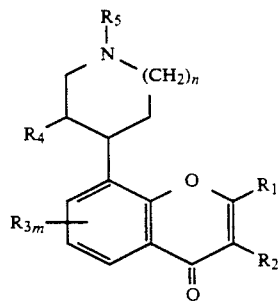

and is defined as follows:

$R_1$ is hydrogen, alkyl having 1 to 6 carbon atoms, aryl-$C_1$-$C_4$-alkyl, substituted $C_1$-$C_6$-alkyl, $C_3$-$C_8$-cycloalkyl, a $C_3$-$C_8$-heterocyclic ring having 1, 2 or 3 hetero atoms, such as N, S, O or any combinations thereof, or else $C_3$-$C_8$-cycloalkyl-$C_1$-$C_4$-alkyl, $C_2$-$C_6$-alkenyl, $C_2$-$C_6$-alkynyl, aryl including polycyclic rings, or aromatic heterocyclic radicals, substituted aryl, carboxyl or an aldehyde or COO—$C_1$-$C_4$-alkyl group, a primary amino, alkylamino, aralkylamino, dialkylamino, amido, arylamino or diarylamino group, or —$CH_2O$—$C_1$-$C_4$-alkyl;

$R_2$ is hydrogen, alkyl having 1 to 6 carbon atoms, aryl, nitro, amino, di-$C_1$-$C_1$-$C_4$-alkylamino or a halogen, or hydroxyl, alkoxy, —COOH, —COO—$C_1$-$C_4$-alkyl, —CHO, —$CH_2OH$ or —$CH_2O$—$C_1$-$C_4$-alkyl;

$R_3$ is hydrogen, $C_1$-$C_4$-alkyl, substituted $C_1$-$C_4$-alkyl, hydroxyl, carboxyl, $C_1$-$C_4$-alkyl, nitro, amino, a $C_1$-$C_4$-alkylamino or di-$C_1$-$C_4$-alkylamino group, or

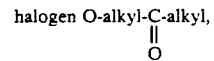

—CHO, —$CH_2OH$, —$CH_2O$—$C_1$-$C_4$-alkyl,

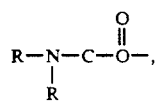

where R is H, $C_1$-$C_4$-alkyl, cycloalkyl and aryl;

$R_4$ is hydrogen, hydroxyl, $C_1$-$C_4$-alkoxy, $C_1$-$C_4$-alkanoyloxy, $C_1$-$C_4$-alkoxycarbonyl, aryloxy or amino, or a $C_1$-$C_4$-alkylamino or di-$C_1$-$C_4$-alkylamino group, or is

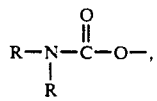

where R is H, C$_1$-C$_6$-alkyl,

or aryl;

R$_5$ is hydrogen, C$_1$-C$_6$-alkyl, aryl-C$_1$-C$_4$-alkyl, C$_3$-C$_8$-cycloalkyl, C$_3$-C$_8$-cycloalkyl-C$_1$-C$_4$-alkyl, alkylamino, C$_1$-C$_4$-alkanoyl,

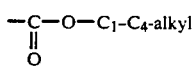

or aroyl, where the aryl group is unsubstituted or mono- or polysubstituted phenyl;

m is an integer between 0 and 3 and n is an integer between 0 and 2, and pharmacologically acceptable acid addition salts thereof.

The compounds according to the invention have two centers of asymmetry, one where the heterocyclic ring containing nitrogen is fused to the benzopyran moiety (C-4'), the other at the R$_4$-substituted carbon atom (C-3'), which means that two pairs of optical isomers are possible. The definition of the compounds according to the invention embraces all possible stereoisomers and their mixtures. It very particularly embraces the racemic forms and the isolated optical isomers having the specified activity. The two racemates can be resolved by physical methods, such as, for example, fractional crystallization. The individual optical isomers can be obtained from the racemates by conventional methods, such as, for example, salt formation with an optically active acid followed by crystallization.

Examples of alkyl groups which are suitable for R$_1$ to R$_5$ are straight-chain or branched radicals having up to 6, preferably up to 5, carbon atoms, for example methyl, ethyl, propyl, isopropyl, t-butyl, pentyl or isopentyl groups.

Examples of substituted alkyl groups which are suitable for R$_1$ to R$_5$ are haloalkyl, such as trifluoromethyl, hydroxyalkyl, such as hydroxyethyl, or carboxyalkyl, such as carboxyethyl.

Suitable examples of a cycloalkyl group which has 3 to 6 carbon atoms and is represented by R$_1$ and R$_5$ are cyclopropyl, cyclobutyl, cyclopentyl or cyclohexyl. Cyclopropylmethyl is an example of cycloalkylalkyl.

An example of an aralkyl group which is represented by R$_1$ and R$_5$ is a phenylalkyl group in which the phenyl group is unsubstituted or monosubstituted or polysubstituted by substituents such as halogen, C$_1$-C$_4$-alkyl, C$_1$-C$_4$-alkoxy or nitro or by a trifluoromethyl group, amino group and substituted amino group.

An example of an aryl group which is represented by R$_1$ and R$_5$ is a phenyl group which is unsubstituted or monosubstituted or polysubstituted by substituents such as halogen, C$_1$-C$_4$-alkyl, C$_1$-C$_4$-alkoxy, hydroxyl, carboxyl, COO alkyl, COHN$_2$, CONH alkyl, CON(alkyl)$_2$, nitro or trifluoromethyl, amino, C$_1$-C$_4$-alkylamino, di-C$_1$-C$_4$-alkylamino, aromatic heterocyclic groups such as pyridyl groups, and polycyclic aromatic radicals, such as naphthyl groups.

A suitable example of an alkylamino group which is represented by R$_1$ and R$_5$ is (CH$_2$)$_n$—NR$_6$R$_7$, where n is 1 to 3 and R$_6$ and R$_7$ are alkyl and are as defined as above in the case of alkyl R$_1$ to R$_5$; moreover, R$_6$ and R$_7$ together with the nitrogen atom to which they are bonded can be a heterocyclic ring having one or more hetero atoms. Suitable examples of heterocyclic rings which are formed by R$_6$ and R$_7$ together with the nitrogen to which they are bonded are piperidine, pyrrolidine, morpholine, piperazine or imidazole, all of which can be unsubstituted or substituted in one or more positions by C$_1$-C$_4$-alkyl, C$_1$-C$_4$-alkoxy or aryl or by a hydroxyl or amino group.

Suitable examples of salts of the compounds according to the invention with inorganic or organic acids are hydrochloride, hydrobromide, sulfate, phosphate, acetate, oxalate, tartrate, citrate, maleate or fumarate.

The use of compounds of the formula Ia

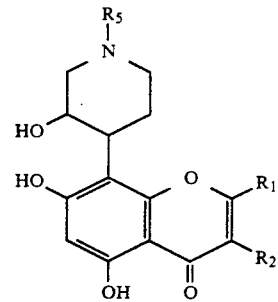

Ia in which

R$_1$ is hydrogen or C$_1$-C$_3$-alkyl, naphthyl, aryl, aralkyl, substituted aryl or a C$_3$-C$_9$-heterocyclic ring, R$_2$ is hydrogen or C$_1$-C$_3$-alkyl, R$_5$ is C$_1$-C$_3$-alkyl or C$_3$-C$_5$-cycloalkyl, or C$_3$-C$_5$-cycloalkyl-C$_1$-C$_4$-alkyl, or of pharmacologically acceptable acid addition salts thereof, is preferred.

The use of compounds of the formula Ia, wherein

R$_1$ is phenyl, thienyl, pyridyl, chlorophenyl, dichlorophenyl, methylphenyl, aminophenyl bromophenyl, hydroxyphenyl or naphthyl, R$_2$ is hydrogen and R$_5$ is methyl, or of pharmacologically acceptable acid addition salts thereof, is very particularly preferred.

Also part of the subject-matter of the invention are the novel compounds of the formula Ib

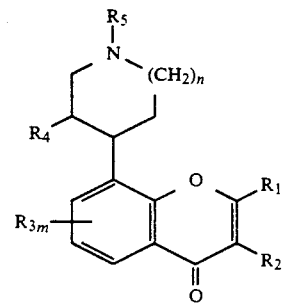

Ib in which at least one of the substituents has one of the meanings below, while the other substituents in each case can be as defined above for formula I:

$R_1$ is $C_3$-$C_6$-cycloalkyl, a $C_3$-$C_9$-heterocyclic ring having 1, 2 or 3 hetero atoms, such as N, S, O or any combinations thereof, or a $C_3$-$C_6$-cycloalkyl-$C_1$-$C_4$-alkyl, or polycyclic rings, aromatic heterocyclic radicals, substituted aryl, aralkyl, a primary amino, alkylamino, aralkylamino, dialkylamino, arylamino or diarylamino group, or —$CH_2O$—$C_1$-$C_4$-alkyl;

$R_2$ is aryl, hydroxyl, alkoxy, COOH, COO—$C_1$-$C_4$-alkyl, —CHO, —$CH_2OH$ or —$CH_2O$—$C_1$-$C_4$-alkyl;

$R_3$ is carboxyl, a halogen, —CHO, —$CH_2OH$, —$CH_2O$—$C_1$-$C_4$-alkyl or

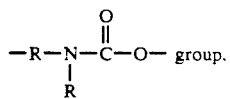

where R is H, $C_1$-$C_6$-alkyl, cycloalkyl and aryl;

$R_4$ is

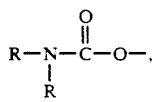

where R is H, $C_1$-$C_6$-alkyl, cycloalkyl or aryl;

$R_5$ is aroyl, where the aryl group is monosubstituted or polysubstituted phenyl, and m is an integer between 0 and 3 and n is an integer between 0 and 2, and pharmacologically acceptable acid addition salts thereof. These compounds can be prepared, for example, as described in European Patent 0,157,193 or in DE 3,612,337.

Examples of preferred compounds according to the invention, or of compounds which are particularly suitable for the use according to the invention, are:

(±)-cis-5,7-dihydroxy-2-(2-thienyl)-8-[4-(3-hydroxy-1-methyl)piperidinyl]-4H-1-benzopyran-4-one, (−)-cis-5,7-dihydroxy-2-phenyl-8-[4-(3-hydroxy-1-methyl)piperidinyl]-4H-1-benzopyran-4-one hydrochloride, (±)-cis-5,7-dihydroxy-2-phenyl-8-[4-(3-hydroxy-1-methyl)piperidinyl]-4H-1-benzopyran-4-one hydrochloride, (+)-cis-5,7-dihydroxy-2-phenyl-8-[4-(3-hydroxy-1-methyl)piperidinyl]-4H-1-benzopyran-4-one hydrochloride, (−)-cis-5,7-dihydroxy-2-(2-pyridyl)-8-[4-(3-hydroxy-1-methyl)piperidinyl]-4H-1-benzopyran-4-one hydrochloride, (±)-cis-5,7-dihydroxy-2-(2-pyridyl)-8-[4-(3-hydroxy-1-methyl)piperidinyl]-4H-1-benzopyran-4-one hydrochloride, (±)-cis-5,7-dihydroxy-2-(3-pyridyl)-8-[4-(3-hydroxy-1-methyl)piperidinyl]-4H-1-benzopyran-4-one hydrochloride, (±)-cis-5,7-dihydroxy-2-(4-pyridyl)-8-[4-(3-hydroxy-1-methyl)piperidinyl]-4H-1-benzopyran-4-one hydrochloride, (−)-cis-5,7-dihydroxy-2-(2-chlorophenyl)-8-[4-(3-hydroxy-1-methyl)piperidinyl]-4H-1-benzopyran-4-one hydrochloride, (+)-cis-5,7-dihydroxy-2-(2-chlorophenyl)-8-[4-(3-hydroxy-1-methyl)piperidinyl]-4H-1-benzopyran-4-one hydrochloride, (±)-cis-5,7-dihydroxy-2-(2-chlorophenyl)-8-[4-(3-hydroxy-1-methyl)piperidinyl]-4H-1-benzopyran-4-one hydrochloride, (±)-cis-5,7-dihydroxy-2-(2,5-dichlorophenyl)-8-[4-(3-hydroxy-1-methyl)piperidinyl]-4H-1-benzopyran-4-one hydrochloride, (±)-cis-5,7-dihydroxy-2-(2,4-dichlorophenyl)-8-[4-(3-hydroxy-1-methyl)piperidinyl]-4H-1-benzopyran-4-one hydrochloride, (±)-cis-5,7-dihydroxy-2-(4-methylphenyl)-8-[4-(3-hydroxy-1-methyl)piperidinyl]-4H-1-benzopyran-4-one hydrochloride, (±)-cis-5,7-dihydroxy-2-(3-methylphenyl)-8-[4-(3-hydroxy-1-methyl)piperidinyl]-4H-1-benzopyran-4-one hydrochloride, (±)-cis-5,7-dihydroxy-2-(4-aminophenyl)-8-[4-(3-hydroxy-1-methyl)piperidinyl]-4H-1-benzopyran-4-one hydrochloride, (±)-cis-5,7-dihydroxy-2-(3-bromophenyl)-8-[4-(3-hydroxy-1-methyl)piperidinyl]-4H-1-benzopyran-4-one hydrochloride, (±)-cis-5,7-dihydroxy-2-(2-naphthyl)-8-[4-(3-hydroxy-1-methyl)piperidinyl]-4H-1-benzopyran-4-one hydrochloride, (±)-cis-5,7-dihydroxy-2-(4-hydroxyphenyl)-8-[4-(3-hydroxy-1-methyl)piperidinyl]-4H-1-benzopyran-4-one and (±)-cis-5,7-dihydroxy-2-(2-hydroxyphenyl)-8-[4-(3-hydroxy-1-methyl)piperidinyl]-4H-1-benzopyran-4-one.

Other 4H-1-benzopyran-4-one derivatives according to the invention or compounds according to the invention which are particularly suitable for the use according to the invention are listed in Tables 1 and 2 below together with their physical data. Table 1 relates to formula Ic

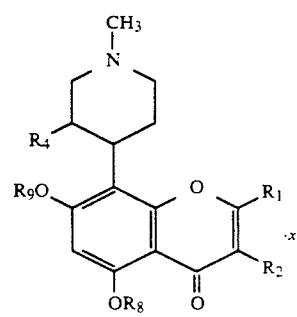

and Table 2 relates to formula Id

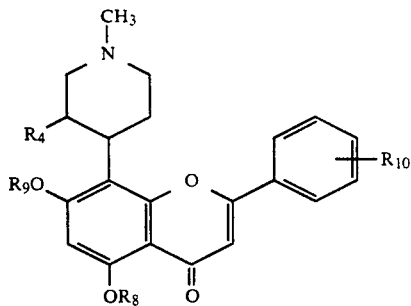

TABLE 1

| Verb. | R₁ | R₂ | R₄ | R₈ | R₉ | X | Melting point (°C.) | Optical rotation |
|---|---|---|---|---|---|---|---|---|
| 1 | H | H | OH | H | H | — | 298 (decomp.) | (±) |
| 2 | H | H | OH | CH₃ | CH₃ | HCl, 1.5H₂O | 173-175 | (±) |
| 3 | CH₃ | H | OH | H | H | HCl, | 237-240 | (±) |
| 4 | CH₃ | H | OH | H | H | HCl, | 241-43 | (+) |
| 5 | CH₃ | H | OH | H | H | HCl, | 241-42 | (−) |
| 6 | CH₃ | H | OH | H | CH₃ | HCl, | 230-232 | (±) |
| 7 | CH₃ | H | OH | CH₃ | CH₃ | 2HCl, 2H₂O | 236-239 | (±) |
| 8 | CH₃ | H | H | H | H | H₂O | 232-233 | (±) |
| 9 | C₂H₅ | H | OH | H | H | HCl, 1.5H₂O | 230-233 | (±) |
| 10 | C₂H₅ | H | OH | CH₃ | CH₃ | HCl, 1.5H₂O | 240-242 | (±) |
| 11 | n-C₃H₇ | CH₃ | OH | H | H | — | 191-192 | (±) |
| 12 | n-C₃H₇ | H | OH | H | H | HCl, | 190-192 | (±) |
| 13 | n-C₃H₇ | H | OH | H | H | HCl, 0.5H₂O | 197-200 | (+) |
| 14 | n-C₃H₇ | H | OH | H | H | HCl, 0.5H₂O | 198-201 | (−) |
| 15 | n-C₄H₉ | H | OH | H | H | HCl, H₂O | 157-159 | (±) |
| 16 | CH₃ | CH₃ | OH | H | H | H₂O | 232-233 | (±) |
| 17 | 2-Pyridyl | H | OH | H | H | HCl, 0.5H₂O | 229° C. | (±) |
| 18 | 3-Pyridyl | H | OH | H | H | 2HCl, 2H₂O | 278-280 | (±) |
| 19 | 4-Pyridyl | H | OH | H | H | 2HCl, 1.5H₂O | 236-238 | (±) |
| 20 | CO₂H | H | OH | CH₃ | CH₃ | H₂O | >340 | (±) |
| 21 | 2-Thienyl | H | OH | H | H | 2H₂O | 243-244 | (±) |
| 22 | 2-Thienyl | H | OH | CH₃ | CH₃ | — | 207-208 | (±) |
| 23 | 2-Pyridyl | H | OH | H | H | 2HCl, 2H₂O | 220-228 | (−) |
| 24 | β-Styryl | H | OH | H | H | HCl, 1.5H₂O | >300 | (±) |
| 25 | 1-Naphthyl | H | OH | H | H | HCl, H₂O | 195-200 | (±) |
| 26 | 2-Naphtyl | H | OH | H | H | HCl, 0.5H₂O | 280-282 | (±) |
| 27 | (2-Chloro'phenyl)methyl | H | OH | H | H | HCl | 270-275 | (±) |

TABLE 2

| Verb. | R₁₀ | R₈ | R₉ | X | Melting point (°C.) | Optical rotation |
|---|---|---|---|---|---|---|
| 28 | H | H | H | HCl, 2H₂O | 273-275 | (±)/trans |
| 29 | 4-NO₂ | H | H | HCl, 3H₂O | 249 (decomp.) | (±) |
| 30 | 4-NO₂ | CH₃ | CH₃ | HCl, 2H₂O | 257-260 (decomp.) | (±) |
| 31 | 2-Cl | H | H | HCl, H₂O | 198-200 | (±) |
| 32 | 2-Cl | CH₃ | CH₃ | 1.5HCl, H₂O | 190-191 | (±) |
| 33 | 4-NH₂ | H | H | 2HCl, 2H₂O | 240-242 | (±) |
| 31 | 3,5-Dimethoxy | CH₃ | CH₃ | 2HCl, 2H₂O | 180-182 | (±) |
| 32 | 4-Br | H | H | HCl, 2H₂O | 215 | (±) |
| 33 | 4-Cl | H | H | HCl, 1.5H₂O | 225 | (±) |
| 34 | 2,4-Dichlor | H | H | HCl, 2.5H₂O | 165-166 | (±) |
| 35 | 4-F | H | H | HCl, H₂O | 285-287 | (±) |
| 36 | 2-F | H | H | HCl, 2H₂O | 263-265 | (±) |
| 37 | 4-Methyl | H | H | HCl, 1.5H₂O | 247-49 | (±) |
| 38 | 3,5-Dihydroxy | H | H | HCl, 3H₂O | 300-302 | (±) |
| 39 | 3-Cl | H | H | HCl, 2H₂O | 288-290 | (±) |
| 40 | 3-Methyl | H | H | HCl, 2H₂O | 268 | (±) |
| 41 | 2-Methyl | H | H |  | 204-205 | (±) |
| 42 | 2-Cl | H | H | HCl, 2H₂O | 190-192 | (+) |
| 43 | H | H | H | HCl | 269-271 | (±) |
| 44 | 3-Br | H | H | HCl, 2H₂O | 285 | (±) |
| 45 | 3-CO₂Me | CH₃ | CH₃ | 1.5HCl, 3H₂O | 235 | (±) |
| 46 | 2,5-Dichloro' | H | H | HCl, H₂O | 251-252 | (±) |
| 47 | 3-COOH | CH₃ | CH₃ | HCl, 1.5H₂O | 270 | (±) |
| 48 | 2-Cl | H | H | HCl, 1.5H₂O | 190-194 | (−) |
| 49 | H | H | H | HCl, 0.5H₂O | 266-269 | (−) |
| 50 | H | H | H | HCl | 270-271 | (+) |
| 51 | 4-OH | H | H | H₂O | >340 | (±) |
| 52 | 4-Phenyl | H | H | HCl | 240-242 | (±) |
| 53 | 2-Br | H | H | 1.5H₂O | 250-252 | (±) |
| 54 | 2-OH | H | H | H₂O | 265-270 | (±) |

The preparation of some of the compounds which can be used according to the invention and the preparation of the necessary starting materials are described in detail in German Offenlegungsschrift 3,612,337, to which reference is made at this point. Another subject-matter of the present invention is a process for the preparation of the novel compounds of the formula Ib as defined above. In this process, a compound of the formula II

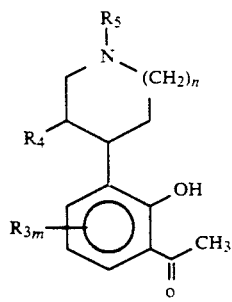

II

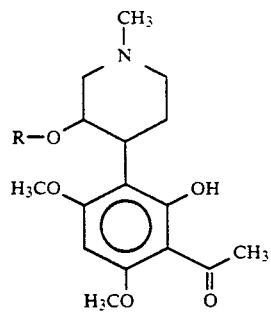

IV where R₄ is hydroxyl or acetoxy and $R_3$, $R_5$, n and m are as defined, is reacted, for example with an alkali metal and the alkyl ester of an acid of the formula $R_1$—COOalkyl, where $R_1$ is as defined in formula I, to give a diketone of the formula III

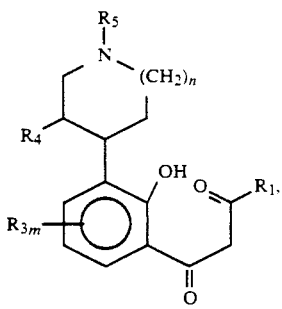

III and the resulting compound is cyclized by reaction with a mineral acid to give a compound of the formula Ib, where $R_1$, $R_3$, $R_5$, m and n are as defined, $R_4$ is the hydroxyl or acetoxy group and $R_2$ is hydrogen, and, if appropriate, a compound of the formula Ib where $R_5$ is $CH_3$ is reacted with cyanogen bromide after the hydroxyl groups have been protected, and the resulting compound is reacted under acid or alkaline conditions to give a compound of the formula Ib where $R_5$ is hydrogen, and, if appropriate, a compound of the formula Ib where $R_5$ is hydrogen is reacted with suitable electrophilic reagents, such as halides, acid chlorides, tosylates or enones, to give compounds of the formula Ib where $R_5$ is unsubstituted or substituted $C_1$-$C_6$-alkyl, aryl-$C_1$-$C_4$-alkyl, $C_3$-$C_6$-cycloalkyl or $C_3$-$C_6$-cycloalkyl-$C_1$-$C_4$-alkyl, and, if appropriate, a compound of the formula Ib where $R_2$ is hydrogen is reacted with a secondary amine hydrochloride and paraformaldehyde to give a compound of the formula Ib where $R_2$ is dialkylaminomethyl, or, if appropriate, a compound of the formula Ib where $R_2$ is hydrogen is nitrated to give a compound of the formula Ib where $R_2$ is $NO_2$, and, if appropriate, a compound of the formula Ib where $R_2$ is $NO_2$, is hydrogenated to give a compound of the formula Ib where $R_2$ is the amino group.

The conditions for the individual reaction steps are as described in German Offenlegungsschrift 3,612,337. A particularly preferred method for the preparation of compounds according to the invention is the reaction of a compound of the formula IV in which R is —$COCH_3$ or H, with a compound of the formula $R_1$—COO X in which X is hydrogen or halogen, preferably hydrogen or chloride. This esterification takes place under generally known conditions, as described, for example, in Organikum [Laboratory Practice in Organic Chemistry], VEB, Deutscher Verlag der Wissenschaften, 15th edition, Berlin 1977, Chapter D7. The resulting esters are treated in an inert atmosphere with bases, for example sodium hydride, or preferably in aprotic solvents, for example tetrahydrofuran, dioxane or N,N-dimethylformamide, this giving diketones which are usually not isolated. On stirring with a mineral acid, for example HCl, the ketone cyclize, and benzopyran-4-one derivatives of the formula Ib are formed. The process is widely applicable and is particularly useful for the preparation of compounds such as formula Ib where $R_1$ is aryl and heteroaryl groups. The above reaction will be illustrated in greater detail in the Examples.

The compounds according to the invention have pharmacological properties; in particular, they inhibit oncogene-encoded kinases, such as tyrosin kinase, serin/threonin kinase and growth factor receptor tyrosin kinase, and it can therefore be expected that they inhibit growth and spreading of tumors and that they can be used in the therapy of tumors.

Further subject-matter of the invention are therefore also pharmaceuticals for controlling tumors, which contain at least one compound of the formula I as defined above or at least one of its pharmacologically acceptable acid addition salts, and the use of a compound of the formula I as defined above for the preparation of a pharmaceutical having an antitumoral action.

The 4H-1-benzopyran-4-one derivatives are used according to the invention in the generally known fashion which is known to the expert. For pharmaceuticals, an effective amount of the active substance mentioned is employed either per se or preferably in combination with suitable pharmaceutical auxiliaries in the form of tablets, coated tablets, capsules, suppositories, emulsions, suspensions or solutions, the active compound content being up to about 95%, preferably between 10 and 75%.

The expert will know which auxiliaries are suitable for the desired formulation of the pharmaceutical because of his expert knowledge. Besides auxiliaries for tablets, or solvents, gel formers, bases for suppositories, and other excipients for the active substance, it is possible to use, for example, antioxidants, dispersants, emulsifiers, defoamers, flavor corrigants, preservatives, solubilizers or colorants.

The active substance can be administered orally, parenterally, intravenously or rectally, intravenous administration being preferred. For a form of oral administration, the active substance may be mixed with other compounds together with the additives which are suitable for this purpose, such as excipients, stabilizers or inert diluents, and customary methods can be used for bringing it into suitable administration forms, such as tablets, coated tablets, hard-gelatin capsules, and aqueous alcoholic or oily suspensions or solutions. Examples of inert excipients which can be used are gum arabic, magnesia, lactose, glucose or starch, in particular corn starch. In this context, the formulation can be prepared as dry granules or moist granules. Examples of suitable oily excipients or solvents are vegetable or animal oils, such as sunflower oil or codliver oil.

For subcutaneous or intravenous administration, a solution, suspension or emulsion of the active substance is formed, if appropriate using substances which are conventional for this purpose, such as solubilizers, emulsifiers or other auxiliaries. Examples of suitable solvents are water, physiological sodium chloride solution or alcohols, for example, ethanol, propanol or glycerol, and also sugar solutions, such as glucose solutions or mannitol solutions, or a mixture of the various solvents which have been mentioned.

The dose of 4H-1-benzopyran-4-one derivatives which is to be administered can cover a wide range. The dose to be administered daily is to be selected to suit the desired effect. About 20 to 1,000 mg are preferably administered daily per patient, preferably intravenously. If required, higher or lower daily doses can also be administered, but a maximum amount of 2,000 mg should only be exceeded for a short time.

The pharmacological properties of the compounds mentioned are confirmed by the pharmacological assays which follow and which have been carried out with compounds according to the invention and their salts; the results obtained are listed in Table III.

TEST METHODS

Tyrosin Kinase Inhibition Assays

Testing Procedure:

In the case of tyrosin kinase activity, the starting material was the rat tumor cell line RR 1022 (ATCC CCL47) which had been grown in RPMI 1640 medium + 10% of FCS. This cell line has been transformed with RSV (Rous sarcoma virus) and contains the oncogene product $PP60^{v-src}$, which has tyrosin kinase activity.

The cells were grown until nearly confluent, washed with PBS (phosphate-buffered saline), scraped off from the culture bottle and repeatedly washed twice (0.85% strength NaCl solution) and centrifuged (200× g).

100 μl of buffer (10% of glycerol, 25 mM of Tris-HCl pH 7.4, 10 mM of KCl, 1 mM of EDTA, 1% of ®Triton X-100, surfactant manufactured by Rohm & Haas, Philadelphia, USA, 2 mM PMSF (phenylmethyl sulfonyl fluoride), 100 kallikrein-inactivating units of aprotinin/ml, 2 mM of dithiotreitol) were then added per $1 \times 10^5$ cells in order to lyze the cells. After 5' at 4° C., the lyzate was centrifuged at 10,000× g for 10', and the supernatant was used as a starting material for tyrosin kinase activity.

Tyrosin kinase activity of the lyzate was measured with poly(Glu, Tyr), 4:1, as a substrate. The inhibitor was preincubated with cell lyzate, substrate (2 mg/ml) and $Mg^{2+}$ (10 mM) in 100 mM of HEPEA (N-2-hydroxyethylpiperazin-N'-2-ethanesulfonic acid), pH 7.2, and the reaction was initiated by adding $\gamma$-$^{32}P$ ATP (40 μM). After 15' at 30° C., the substrate was precipitated using 10% strength TCA (trichloroacetic acid), filtered over a Millititer Filtration Plate (Millipore Corporation, Mass., USA), washed and dried. The incorporation of $^{32}P$ was determined by means of a liquid scintillation counter.

Results:

The substances were tested at a maximum concentration of 45 μg/ml and diluted stepwise in the ratio 1:10. $IC_{50}$ denoted the concentration at which 50% of the initial enzyme activity were inhibited (see Table III).

Assay for 3', 5'-cAMP-Dependent Protein Kinase Inhibition

Procedure:

The catalytic sub-unit of cAMP-dependent protein kinase (Sigma) was reconstituted as described by Sigma (Sigma Chemical Co., St. Louis, Mo., USA). The enzyme activity was measured with kemptide (Sigma) (Leu-Arg-Arg-Ala-Ser-Leu-Gly) as the substrate. The inhibitor was preincubated with the enzyme, substrate (190 μM), $Mg^{2+}$ (5 mM), 0.25 mg/ml of BSA and 3.75 mM of mercaptoethanol in 50 mM of MOPA (4-morpholinopropanesulfonic acid), pH 6.9. The reaction was initiated by adding $\gamma$-$^{32}P$ ATP (40 μM). After 15 minutes at 30° C., an aliquot amount was transferred to p81 ion exchange paper (2×2 cm; Whatman Paper Ltd., Great Britain), the paper was immersed in 75 mM $H_3PO_4$, washed and dried, and the incorporation of $^{32}P$ was determined by means of a liquid scintillation counter.

Results:

The results are expressed as % inhibition of the initial enzyme activity at an inhibitor concentration of 45 μg/ml (see Table III).

TABLE III

Formula 1c where $R_2 = R_8 = H$ and $R_4 = OH$

| $R_1$ | X | Sign of the optical rotation | $IC_{50}$ in μg/ml pp60 v-src | % inhibition of cAMP-dependent protein kinase at an inhibitor concentration of 45 μg/ml |
|---|---|---|---|---|
| 2-thiophenyl | — | (±) | 1,7 | 14 |
| 2-bromophenyl | — | (±) | 22,3 | 63 |
| (2-chlorophenyl)-methyl | HCl | (±) | >45,0 | 69 |
| phenyl | HCl | (−) | 5,7 | 46 |
| 2-chlorophenyl | HCl | (+) | 9,2 | 27 |
| 2-fluorophenyl | HCl | (±) | 28,0 | 0 |
| 4-methylphenyl | HCl | (±) | 2,7 | 55 |
| 3-pyridyl | HCl | (±) | 10,6 | 0 |
| 2-pyridyl | HCl | (±) | 34,8 | 0 |
| phenyl | HCl | (+) | 0,7 | 13 |
| 4-pyridyl | HCl | (±) | 4,2 | 12 |
| n-propyl | HCl | (±) | 45,0 | 0 |
| 2-chlorophenyl | HCl | (±) | 3,3 | 29 |
| ethyl | HCl | (±) | >45,0 | 0 |
| phenyl | HCl | (±) | 1,9 | 48 |
| 4-bromophenyl | HCl | (±) | 3,4 | 65 |
| 4-biphenyl | HCl | (±) | 39,0 | 37 |
| n-butyl | HCl | (±) | 0,0 | n.b. |
| 2-pyridyl | HCl | (−) | 7,8 | 6 |
| 2-naphthyl | HCl | (±) | 3,4 | 0 |
| 4-fluorophenyl | HCl | (±) | 2,7 | 25 |
| 4-chlorophenyl | HCl | (±) | 1,6 | 37 |
| n-propyl | HCl | (−) | >45,0 | 5 |

The Example below illustrates the invention without restricting its scope.

SRC Tumor Test

Single cell suspensions (from cell culture A 549 or disaggregated human tumor xenografts LXF 529) in Beriplast (Behringwerke AG) were diluted 1:2 with RPMI 1640 supplemented with 15% FCS to a final cell concentration of $10^7$ cells/50 μl. This suspension was sucked quickly into 50 μglass capillaries (diameter 1.5 mm), of which the inner walls had been moistered with a thrombin/CaCl$_2$ solution (500 units thrombin in 1 ml 40 mmol CaCl$_2$).

After solidification of the cell-fibrin mixture (about 5 min at RT) the fibrin clot has been removed from the glass capillary into a petridish by air pressure. The fibrin clot was cut into 2 mm pieces ($\approx 5 \times 10^5$ cells per piece) and the pieces were stored in RPMI 1640 supplemented with 15% FCS until implantation.

A single fibrin piece was transferred under the renal capsule of a nude mouse and, subsequently, two perpendicular diameters of the implanted piece were measured by microscope with an ocular micrometer (day 0). The tumor size was calculated according to $$V = a \times b$$

V = tumor size
a = largest diameter
b = diameter perpendicular to a

The substance was given i.v. or p.o. daily on day 2–15 with the maximal tolerable dose (MTD) and a dose 2/3 of the MTD value according to the pretests. 5 mice/group were used.

On day 21 after implantation the animals were sacrificed, the kidney was exteriorized and the tumor size was measured again. The effectivity of the test drug was calculated from the tumor growth inhibition.

The relative tumor size $V_R$ was calculated according the formula $$V_R = \frac{V_t}{V_0}$$

$V_t$ = tumor size at the end of experiment (day 21)
$V_0$ = tumor size as day of implantation Subsequently the median relative tumor size of the treated group ($V_T$) was related to the corresponding median relative tumor size of controls ($V_C$) according to the formula $$T/C\ \% = \frac{V_T}{V_C} \times 100$$

The statistical significance (p 0.05) of the antitumoral effects was calculated using the Wilcoxon U test.

Table IV shows the test results

TABLE IV

| compound | tumor | dose (mg/kg/day) | schedule (days) | T/C (%) |
|---|---|---|---|---|
| | bronchogenic carcinomas | | | |
| (Exmp. 17) | LXF 529 | 25 i.v. | 2-15 | 81 n.s. |
| | | 35 i.v. | 2-15 | 67 |
| | A 549 | 35 i.v. | 2-15 | 70 |
| | | 100 p.o. | 2-15 | 73 |
| (Exmp. 9) | LXF 529 | 2 i.v. | 2-15 | 59 |
| | | 4 i.v. | 2-15 | 51 |
| (Exmp. 19) | LXF 529 | 100 i.v. | 2-15 | 98 n.s. |

TABLE IV-continued

| compound | tumor | dose (mg/kg/day) | schedule (days) | T/C (%) |
|---|---|---|---|---|
| | | 150 i.v. | 2-15 | 80 | n.s. = not significant (P > 0.05)

EXAMPLE 1

(+/−)-cis-5,7-dimethoxy-2-(2-thienyl)-8-[4-(3-acetoxy-1-methyl)piperidinyl]-4H-1-benzopyran-4-one 2Thiophenecarboxylic acid (2.73 g) was added at 0° C. to a solution of (±)-cis-3-acetoxy-1-methyl-4- (3-acetyl-4,6-dimethoxy-2-hydroxy)phenylpiperidine of the formula IV, R=COCH$_3$, (3.0 g) in dry pyridine (30 ml), and POCL$_3$ (2.2 ml) was then added. The reaction mixture was stirred for two hours at room temperature. Water (50 ml) was added slowly to the reaction mixture, and the reaction solution was later rendered alkaline by adding sodium carbonate (pH 8). The reaction mixture was extracted using ethyl acetate (3×40 ml). The combined organic extracts were washed with water, dried over anhydrous sodium sulfate, and the solvent removed in vacuo. The residue was chromatographed on silica gel (4% of MeOH in CHCl$_3$); yield 2.7 g of (±)-cis-3-acetoxy-1-methyl-4-(3-acetyl-4,6-dimethoxy-2-(2-thienyloxy)phenyl)piperidine; melting point 153°-154° C.

This compound was taken up in dry dioxane (50 ml), sodium hydride (5 equivalents) was added, and the mixture was stirred for four hours at 40° C. MeOH (10 ml) was added to destroy the excess sodium hydride, and dry HCL gas was passed in until the pH of the solution was clearly acid. The reaction mixture was worked up by adding ice-cold sodium carbonate solution, and the resulting solid product was separated by filtration. Further purification was by means of column chromatography (silica gel, 2% of MeOH, 1% of NH$_4$OH in CHCl$_3$), and (+)-cis-5,7-dimethoxy-2-(2-thienyl)-8-[4-(3-acetoxy-1-methyl)piperidinyl]-4H-1-benzopyran-4-one were obtained. Yield 2.50 g, melting point 207°-208° C.

The following compounds were prepared analogously to Example 1:

EXAMPLE 2

(±)-cis-7,5-Dihydroxy-2-(phenyl)-8-[4-(3-hydroxy-1-methyl)piperidinyl]-4H-1-benzopyran-4-one hydrochloride.

EXAMPLE 3

(−)-cis-5,7-Dihydroxy-2-phenyl-8[-(4-3-hydroxy-1-methyl)-piperidinyl]-4H-1-benzopyran-4-one hydrochloride.

EXAMPLE 4

(±)-cis-5,7-Dihydroxy-2-phenyl -8-[4-(3-hydroxy-1-methyl)-piperidinyl]-4H -1-benzopyran-4-one hydrochloride.

EXAMPLE 5

(−)-cis-5,7-Dihydroxy-2-(2-pyridyl)-8-[4-(3-hydroxy-1-methyl)piperidinyl]-4H-1-benzopyran-4-one hydrochloride.

EXAMPLE 6

(±)-cis-5,7-Dihydroxy-2-(2-pyridyl)-8-[4-(3-hydroxy-1-methyl)piperidinyl]-4H-1-benzopyran-4-one hydrochloride.

EXAMPLE 7

(±)-cis-5,7-Dihydroxy-2-(3-pyridyl)-8-[4-(3-hydroxy-1-methyl)piperidinyl]-4H-1-benzopyran-4-one hydrochloride.

EXAMPLE 8

(±)-cis-5,7-Dihydroxy-2-(4-pyridyl)-8-[4-(3-hydroxy-1-methyl)piperidinyl]-4H-1-benzopyran-4-one hydrochloride.

EXAMPLE 9

(−)-cis-5,7-Dihydroxy-2-(2-chlorophenyl)-8-[4-(3-hydroxy-1-methyl)piperidinyl]-4H-1-benzopyran-4-one hydrochloride.

EXAMPLE 10

(+)-cis-5,7-Dihydroxy-2-(2-chlorophenyl)-8-[4-(3hydroxy-1-methyl)piperidinyl]-4H-1-benzopyran-4-one hydrochloride.

EXAMPLE 11

(±)-cis-5,7-Dihydroxy-2-(2-chlorophenyl)-8-[4-(3-hydroxy-1-methyl)piperidinyl]-4H-1-benzopyran-4-one hydrochloride.

EXAMPLE 12

(±)-cis-5,7-Dihydroxy-2-(2,5-dichlorophenyl)-8-[4-(3-hydroxy-1-methyl)piperidinyl]-4H-1-benzopyran-4-one hydrochloride.

EXAMPLE 13

(±)-cis-5,7-Dihydroxy-2-(2,4-dichlorophenyl)-8-[4-(3-hydroxy-1-methyl)piperidinyl]-4H-1-benzopyran-4-one hydrochloride.

EXAMPLE 14

(±)-cis-5,7-Dihydroxy-2-(4-methylphenyl)-8-[4-(3-hydroxy-1-methyl)piperidinyl]-4H-1-benzopyran-4-one hydrochloride.

EXAMPLE 15

(±)-cis-5,7-Dihydroxy-2-(4-methylphenyl)-8-[4-(3-hydroxy-1-methyl)piperidinyl]-4H-1-benzopyran-4-one hydrochloride.

EXAMPLE 16

(±)-cis-5,7-Dihydroxy-2-(4-aminophenyl)-8-[4-(3-hydroxy-1-methyl)piperidinyl]-4H-1-benzopyran-4-one hydrochloride.

EXAMPLE 17

(±)-cis-5,7-Dihydroxy-2-(3-bromophenyl)-8-[4-(3-hydroxy-1-methyl)piperidinyl]-4H-1-benzopyran-4-one hydrochloride.

EXAMPLE 18

(±)-cis-5,7-Dihydroxy-2-(2-naphthyl)-8-[4-(3-hydroxy-1-methyl)piperidinyl]-4H-1-benzopyran-4-one hydrochloride.

EXAMPLE 19

(±)-cis-5,7-Dihydroxy-2-(4-hydroxyphenyl)-8-[4-(3-hydroxy-1-methyl)piperidinyl]-4H-1-benzopyran-4-one.

EXAMPLE 20

(±)-cis-5,7-Dihydroxy-2-(2-hydroxyphenyl)-8-[4-(3-hydroxy-1-methyl)piperidinyl]-4H-1-benzopyran-4-one.

EXAMPLE 21

Active substance solutions which are suitable for injection contain the constituents mentioned below and can be prepared in a manner known per se by mixing the substances with each other and filling sterile ampoules with the solutions. The solutions for injections are used for the treatment of tumors in a dose of 1–2 injection units (1 injection unit = 1 ampoule) per day.

| Constituents (per ampoule) | Weight |
|---|---|
| (±)-cis-5,7-Dimethoxy-2-(2-thienyl-8-[4-(3-acetoxy-1-methyl)piperidinyl]-4H-1-benzopyran-4-one | 200 mg |
| Sodium chloride | 50 mg |
| Methylparaben | 5 mg |
| Sterile water | 5 mg |

We claim:

1. A method of inhibiting oncogene-encoded kinases or growth factor receptor tyrosin kinases comprising administering to a patient an effective amount of a compound of the formula I

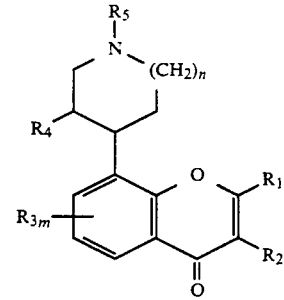

in which $R_1$ is hydrogen, alkyl having 1 to 6 carbon atoms, aryl-$C_1$–$C_4$-alkyl; $C_1$–$C_6$-alkyl substituted by halogen, hydroxy, or carboxy; $C_3$–$C_6$-cycloalkyl, pyridyl, thienyl, $C_3$–$C_6$-cycloalkyl-$C_1$–$C_4$-alkyl, $C_2$–$C_6$-alkenyl, $C_2$–$C_6$-alkynyl, phenyl; phenyl, mono- or polysubstituted by halogen, $C_1$–$C_4$-alkyl, $C_1$–$C_4$-alkoxy, hydroxyl, carboxyl, COO-alkyl, CONH$_2$, CONH-alkyl, CON(alkyl)$_2$, nitro, trifluoromethyl, amino, $C_1$–$C_4$-alkylamino, di-$C_1$–$C_4$-alkylamino, or phenyl; naphthyl, carboxyl, —CHO, COO—$C_1$–$C_4$-alkyl, a primary amino, alkylamino, aralkylamino, dialkylamino, amido, arylamino, diarylamino, or —CH$_2$O—$C_1$–$C_4$-alkyl;

$R_2$ is hydrogen, alkyl having 1 to 6 carbon atoms, aryl, nitro, amino, di-$C_1$–$C_4$-alkylamino, a halogen, hydroxyl, alkoxy, —COOH, —COO—$C_1$–$C_4$-alkyl, —CHO, —CH$_2$OH or —CH$_2$O—$C_1$–$C_4$-alkyl;

$R_3$ is hydrogen, $C_1$-$C_4$-alkyl; $C_1$-$C_4$-alkyl substituted by halogen, hydroxy, or carboxy; hydroxyl, carboxyl, nitro, amino, $C_1$-$C_4$-alkylamino, di-$C_1$-$C_4$-alkylamino, halogen,

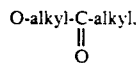

—CHO, —CH$_2$OH, —CH$_2$O—$C_1$-$C_4$-alkyl, or

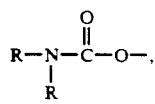

where R is H, $C_1$-$C_6$-alkyl, cycloalkyl,

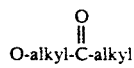

or aryl;

$R_4$ is hydrogen, hydroxyl, $C_1$-$C_4$-alkoxy, $C_1$-$C_4$-alkanoyloxy, $C_1$-$C_4$-alkoxycarbonyl, aryloxy, amino, $C_1$-$C_4$-alkylamino, di-$C_1$-$C_4$-alkylamino, or

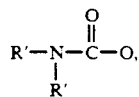

where R' is H, $C_1$-$C_6$-alkyl, cycloalkyl or aryl;

$R_5$ is hydrogen, $C_1$-$C_6$-alkyl, aryl-$C_1$-$C_4$-alkyl, $C_3$-$C_6$-cycloalkyl, $C_3$-$C_6$-cycloalkyl-$C_1$-$C_4$-alkyl, alkylamino, $C_1$-$C_4$-alkanoyl,

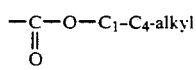

or aroyl, where the aryl group in $R_1$, $R_2$, $R_3$, $R_4$, and $R_5$ is unsubstituted phenyl or phenyl that is mono- or polysubstituted by halogen, $C_1$-$C_4$-alkyl, $C_1$-$C_4$-alkoxy, hydroxyl, carboxyl, COO-alkyl, CONH$_2$, CONH-alkyl, CON(alkyl)$_2$, nitro, trifluoromethyl, amino, $C_1$-$C_4$-alkylamino, di-$C_1$-$C_4$-alkylamino, or phenyl;

m is an integer between 0 and 3 and
n is 1,
or a pharmacologically acceptable acid addition salt thereof.

2. The method of claim 1, wherein the compound has the formula Ia

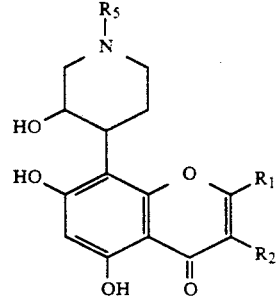

in which $R_1$ is hydrogen, $C_1$-$C_3$-alkyl, naphthyl, phenyl; phenyl mono- or polysubstituted by halogen, $C_1$-$C_4$-alkyl, $C_1$-$C_4$-alkoxy, hydroxyl, carboxyl, COO-alkyl, CONH$_2$, CONH-alkyl, CON(alkyl)$_2$, nitro, trifluoromethyl, amino, $C_1$-$C_4$-alkylamino, di-$C_1$-$C_4$-alkylamino, or phenyl; pyridyl, or thienyl, $R_2$ is hydrogen or $C_1$-$C_3$-alkyl, $R_5$ is $C_1$-$C_3$-alkyl, $C_3$-$C_5$-cycloalkyl, or $C_3$-$C_5$-cycloalkyl-$C_1$-$C_4$-alkyl, or a pharmacologically acceptable acid addition salt thereof.

3. The method of claim 2, in which
$R_1$ is phenyl, thienyl, pyridyl, chlorophenyl, dichlorophenyl, methylphenyl, aminophenyl, bromophenyl, hydroxyphenyl or naphthyl,
$R_2$ is hydrogen and
$R_5$ is methyl,
or a pharmacologically acceptable acid addition salt thereof.

* * * * *

UNITED STATES PATENT AND TRADEMARK OFFICE
CERTIFICATE OF CORRECTION

PATENT NO. : 5,284,856
DATED : February 08, 1994
INVENTOR(S) : Ramchandra G. NAIK et al.

It is certified that error appears in the above-indentified patent and that said Letters Patent is hereby corrected as shown below:

On the title page, Item ]75]
The sixth inventor's name has been omitted; at the end of the listing of inventor's, insert
--;Jorg Czech, Marburg, Fed. Rep. of Germany--.

Signed and Sealed this

Sixth Day of September, 1994

Attest:

BRUCE LEHMAN

Attesting Officer

Commissioner of Patents and Trademarks